United States Patent
Blackwell

(10) Patent No.: US 9,854,851 B2
(45) Date of Patent: *Jan. 2, 2018

(54) THORACIC COMPRESSION BRA

(71) Applicant: Lea M. Blackwell, Fort myers, FL (US)

(72) Inventor: Lea M. Blackwell, Fort myers, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/443,732

(22) Filed: Feb. 27, 2017

(65) Prior Publication Data

US 2017/0202274 A1 Jul. 20, 2017

Related U.S. Application Data

(63) Continuation of application No. 14/943,560, filed on Nov. 17, 2015, now Pat. No. 9,578,902.

(51) Int. Cl.

| | |
|---|---|
| *A41C 3/00* | (2006.01) |
| *A41C 3/02* | (2006.01) |
| *A41F 15/00* | (2006.01) |
| *A61F 5/02* | (2006.01) |
| *A61F 5/03* | (2006.01) |
| *A61M 1/00* | (2006.01) |

(52) U.S. Cl.
CPC .......... *A41C 3/0064* (2013.01); *A41C 3/0028* (2013.01); *A41C 3/0035* (2013.01); *A41C 3/0085* (2013.01); *A41C 3/02* (2013.01); *A41F 15/007* (2013.01); *A61F 5/02* (2013.01); *A61F 5/03* (2013.01); *A61M 1/0009* (2013.01)

(58) Field of Classification Search
CPC ......... A41C 3/148; A41C 3/00; A41C 3/0064; A41C 3/0028; A41C 3/04; A41C 3/005; A41C 3/0057; A41C 3/0021; A41D 1/06; A41D 13/12; A61F 13/145
USPC ........ 450/26, 28, 37, 36, 86, 89, 71, 79, 72, 450/73, 1, 9, 10, 15, 17
See application file for complete search history.

(56) References Cited

U.S. PATENT DOCUMENTS

| | | | |
|---|---|---|---|
| 2,662,522 A | 12/1953 | Muller | |
| 3,561,442 A * | 2/1971 | Goswitz | A61F 5/03 128/DIG. 15 |
| 3,698,399 A | 10/1972 | Hand | |
| 3,968,803 A | 7/1976 | Hyman | |
| 4,369,792 A * | 1/1983 | Miller | A41C 3/148 450/55 |
| 4,804,351 A * | 2/1989 | Raml | A41C 3/0064 2/DIG. 1 |
| 4,949,436 A * | 8/1990 | Anscher | A44B 11/263 24/616 |
| 5,081,718 A * | 1/1992 | Carman | A41D 1/06 2/227 |
| 5,429,593 A * | 7/1995 | Matory | A61F 13/145 2/114 |

(Continued)

*Primary Examiner* — Gloria Hale
(74) *Attorney, Agent, or Firm* — Livingston Loeffler, P.A.; Edward M. Livingston, Esq.; Bryan L. Loeffler, Esq.

(57) ABSTRACT

A thoracic compression bra (1) having an opening located between two portions, a front right portion (2) and a front left portion (3) that are secured together using strap clips (9) that allow pressure being exerted by the bra on a patient to be adjusted. A compression band (24) is located around a circumference of the bra along the lower edge (34) of the bra.

6 Claims, 3 Drawing Sheets

(56) References Cited

U.S. PATENT DOCUMENTS

| | | | | |
|---|---|---|---|---|
| 5,871,388 | A * | 2/1999 | Lambert | A41C 3/02 2/73 |
| 6,168,498 | B1 * | 1/2001 | Wagner | A41C 3/0057 450/1 |
| 6,233,793 | B1 * | 5/2001 | Wanzenbock | A41F 1/006 24/614 |
| D446,629 | S | 8/2001 | Swanger | |
| 6,390,885 | B1 * | 5/2002 | Brooks | A41C 3/0064 450/1 |
| 6,755,717 | B2 | 6/2004 | Smith | |
| 6,793,556 | B1 * | 9/2004 | Fildan | A41C 3/02 2/323 |
| D503,509 | S | 4/2005 | Bell et al. | |
| 7,144,294 | B2 | 12/2006 | Bell et al. | |
| 7,192,409 | B2 * | 3/2007 | Lorenzo | A61F 5/03 2/67 |
| 7,549,971 | B2 | 6/2009 | Bell et al. | |
| 7,775,851 | B2 * | 8/2010 | Sgro | A41C 3/02 450/1 |
| 9,277,773 | B2 * | 3/2016 | Blackwell | A41C 3/0064 |
| 9,578,902 | B2 * | 2/2017 | Blackwell | A41C 3/0064 |
| 2005/0112996 | A1 * | 5/2005 | Buehler | A41F 1/006 450/58 |
| 2011/0318990 | A1 * | 12/2011 | Bodnar | A41C 3/005 450/58 |
| 2014/0302748 | A1 * | 10/2014 | Blackwell | A41C 3/0064 450/58 |

* cited by examiner

THORACIC COMPRESSION BRA

FIELD OF THE INVENTION

This invention relates to compression garments and brassieres and more particularly a bra for providing compressive forces to a female torso and breasts to help prevent wound complications and provide comfort after cardiothoracic surgery.

BACKGROUND OF THE INVENTION

Compression bras are used to help reduce wound complications, provide comfort and chest wall support after cardiothoracic surgeries. The patients who undergo cardiothoracic surgeries, heart bypass, heart valve replacement and lung resections benefit from chest compression. The benefit from the compression bra is to help reduce the swelling after surgery of the chest wall and breasts. The bra supports the breasts for less tension on the sternal incision. If the tension on the skin from the weight of the breasts is sufficient the skin could open causing a wound dehiscence. The dehiscence can increase the infection rates after surgery and cause a prolonged recovery from surgery.

Patients typically require multiple chest tubes after surgery. The chest tubes drain extra fluid from the chest. These tubes are temporary and once they are removed there is an incision from the site of the tube. The bra can facilitate healing of the chest tube sites by protecting the incisions sites from contacting other areas of the skin. Typically, the incisions for the chest tubes are placed where the skin folds and is in contact with other areas of skin. The elastic portion of the inferior aspect of the bra is wide to provide coverage of the entire thoracic cage. The chest tube sites are variable in placement depending on the surgery and the physician choice and the wider elastic support covers the potential incision sites. The wider band around the torso will help prevent movement of the bra and provide stabilization for support. Supporting the breasts after cardiothoracic surgery provides comfort for the patient. The clips on the bra provide adjustability and ease for evaluating the incisions. The mesh for the bra provides ventilation to make the bra cooler, while worn for a prolonged period of time after surgery. Traditionally, the bras do not have elastic to cover the entire thoracic cage and are not made with mesh to help reduce the heat for extended wearing.

SUMMARY OF THE INVENTION

The primary object of the present invention is to provide a thoracic bra that reduces the effects of swelling and bruising commonly experienced after surgery while not causing any discomfort normally experienced with conventional thoracic compression bras.

The present invention fulfills the above and other objects by providing a thoracic bra having an opening located between a front right portion and a front left portion that are secured together using strap clips that allow the pressure being exerted on a patient to be adjusted. The strap clips and adjustable attachment straps offer ergonomic attachments that can easily be secured by a patient having decreased motor function after breast surgery or other surgeries, such as heart surgery. The strap clips and attachment straps allow a patient or caregiver to tighten or loosen the thoracic compression bra by pulling on a distal end of an attachment strap without separating a right front portion of the strap clip from a left front portion of the strap clip, as would be necessary with conventional bras using hook and loop fastener to secure the bra. In addition, strap clips or maternity bra clasps may be used to secure shoulder straps to the front right portion of the bra and the left front portion of the bra.

A drain apron having a plurality of pockets may also be provided to provide storage for drain bulbs. Drain bulbs are reservoirs connected to a flexible drainage tube sutured into place. Drain bulbs remove fluid from the surgical wound through mild suction. The drain apron is worn around a patient's midsection, inferior to and/or extending downward from a lower edge of the bra. Straps extend from side edges of the drain apron and are wrapped around the patient's midsection and back and secured in front of the patient, so the patient does not have to lay on the attachment. A plurality of loops are located along an upper edge of the drain apron. The straps are threaded though the loops to provide additional support to the drain apron and to prevent the drain apron from sagging under the weight of drain bulbs. Elastic is located along an upper edge of each pocket to prevent the drain bulbs from falling out of the apron, which would cause unwanted pulling on the sutures holding the drain tubes in the surgical wound.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
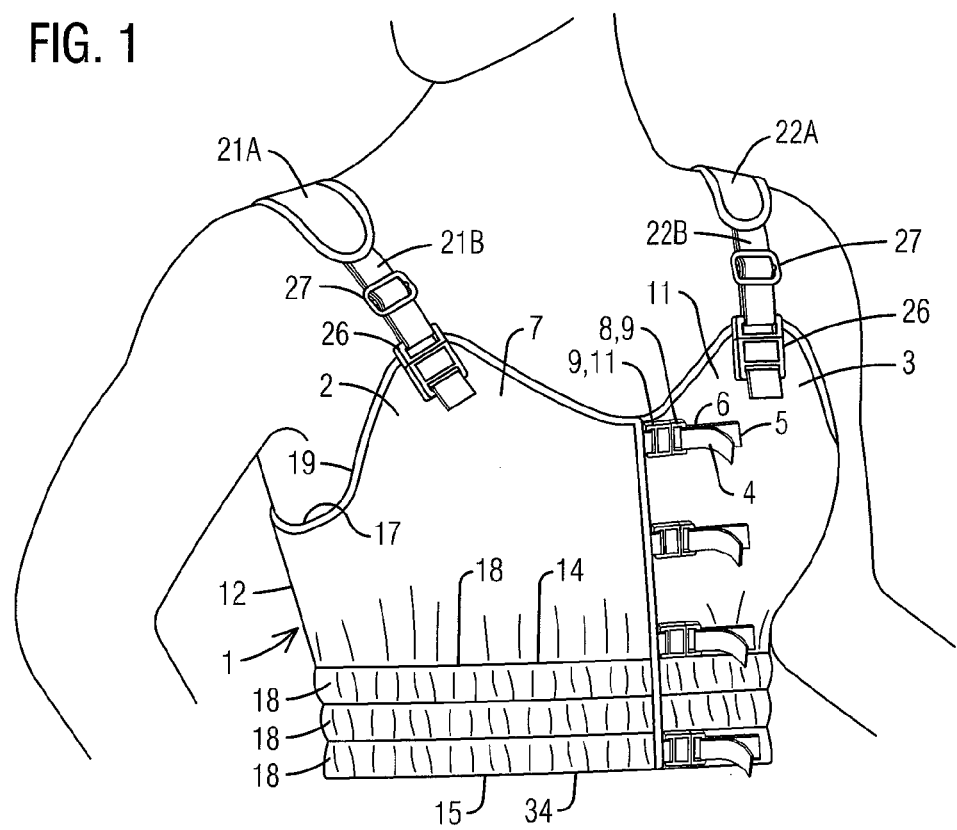
FIG. 1 is a front perspective view of a thoracic compression bra and drain apron of the present invention being worn by a patient.
Figure 2:
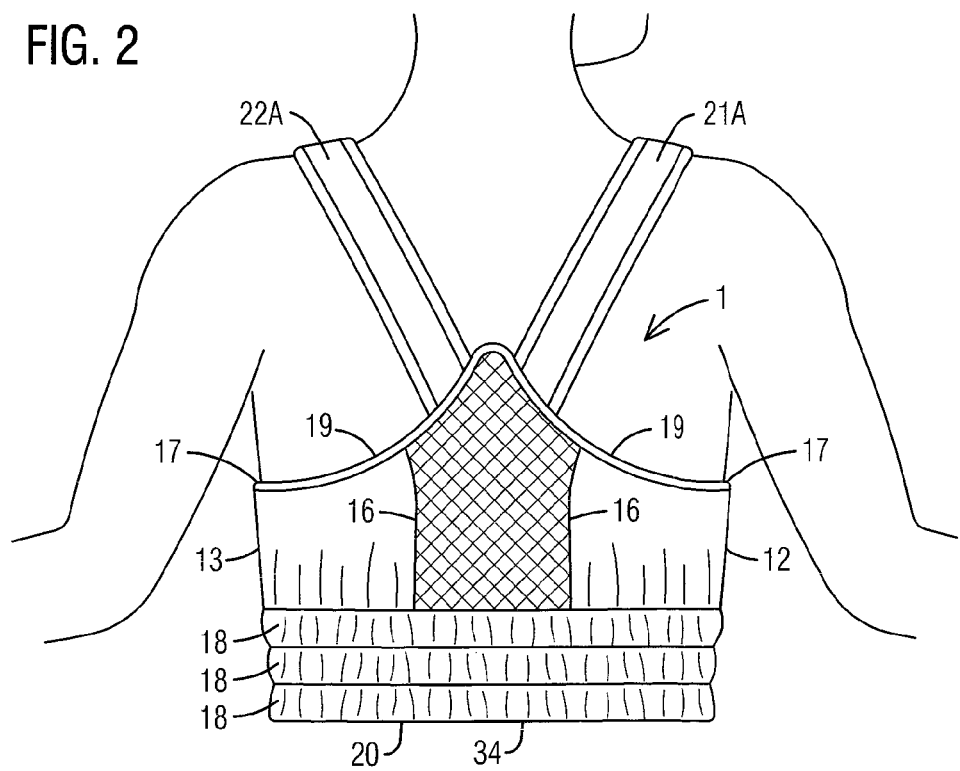
FIG. 2 is a rear view of a thoracic compression bra and drain apron of the present invention being worn by a patient.
Figure 3:
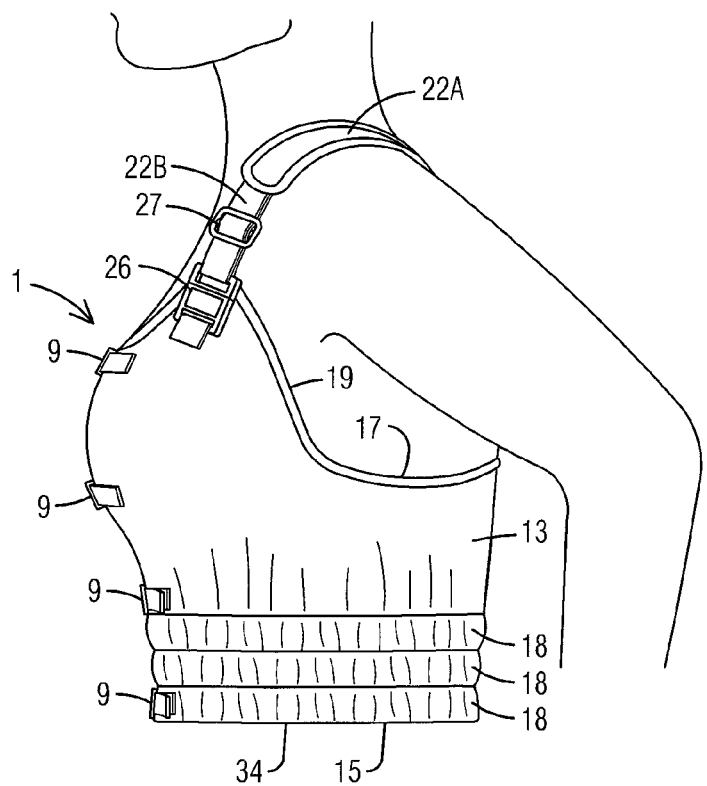
FIG. 3 is a side view of a thoracic compression bra of the present invention having a notch located on a side portion and being worn by a patient.

For purposes of describing the preferred embodiment, the terminology used in reference to the numbered accessories in the drawings is as follows:

1. post operative thoracic compression bra, generally
2. front right portion
3. front left portion
4. attachment strap
5. proximal end
6. distal end
7. front surface of front right section
8. female portion
9. strap clip
10. front surface of front left section
11. male portion 12. right side portion
13. left side portion
14. upper edge of compression band
15. lower edge of compression band
16. rear edge of side portion
17. upper edge of side portion
18. lower edge of side portion
19. angled side edge
20. rear portion
21A. right padded shoulder strap
21B. right adjustable shoulder strap
22A. left padded shoulder strap
22B. left adjustable shoulder strap
23. upper edge of rear portion
24. compression band
25. interior surface
26. maternity clip
27. adjustment clip
28. horizontal section
29. elastic material
30. drain apron
31. pocket
32. drain bulb
33. drain tube
34. lower edge of bra
35. drain apron strap
36. side edge of drain apron
37. attachment means
38. loop
39. upper edge of drain apron
40. main panel of drain apron With reference to FIGS. 1, 2 and 3, a front perspective view of a thoracic compression bra 1 of the present invention being worn by a patient and a rear view of a thoracic compression bra 1 of the present invention being worn by a patient and a side view of a thoracic compression bra 1 of the present invention having an angled side edge 19 a side view of a thoracic compression bra of the present invention having a notch located on a side portion and being worn by a patient located on a side portion and being worn by a patient, respectively, are illustrated. The thoracic compression bra 1 comprises a front right portion 2 and a front left portion 3 that are worn over the patient's breasts. At least one attachment strap 4 having a proximal end 5 and a distal end 6 is attached at the proximal end 6 to a front surface 7 of the front right section 2. A female portion 8 of a strap clip 9 is attached to the distal end 6 of the at least one strap 4 that is attached to the front right portion 2. At least one attachment strap 4 having a proximal end 5 and a distal end 6 is attached at the proximal end 5 to a front surface 10 of the front left portion 3. A male portion 11 of a strap clip 9 is attached to the distal end 6 of the at least one attachment strap 4 that is attached to the front left portion 3. When the front right portion 2 and front left portion 3 are secured together using strap clips 9 a portion of the front left portion 3 rests under a portion of the right front portion 2 to separate the patient's skin from the strap clips 9 and to provide extra cushioning between the patient's skin and the strap clips 9. The strap clips 9 also allow a patient or caregiver to tighten or loosen the thoracic compression bra 1 by pulling on the distal end 6 of the at least one attachment strap 4 without separating the right front portion 2 from the left front portion 3, as would be necessary with conventional bras using hook and loop fastener as an attachment means.

A right side portion 12 and a left side portion 13 extend from an outer edge of the right front portion 2 and the left front portion 3, respectively, around sides of the patient's torso. The side portions 12, 13 each comprise a front edge, rear edge 16, upper edge 17 and lower edge 18. The upper edges 17 of each side portion 12, 13 curves downward toward the lower edges to create substantially angled side edge 19.

A rear portion 20 is located between the rear edges 16 of the side portions 12, 13. The rear portion 20 may be made of a cloth material and/or breathable mesh material that allow airflow to the patient's skin. The rear portion 20 is preferably substantially triangular-shaped and constructed from a mesh material to provide air flow. A right padded shoulder strap 21A and left padded shoulder strap 22A extend from an upper edge 23 of the rear portion 20 over the patient's shoulders. The right padded shoulder strap 21A and the left padded shoulder strap 22A are preferably attached to the front right portion 2 and front left portion 3, respectively, by maternity clips 9 and adjustable shoulder straps 21B, 22B that allow the padded shoulder straps 21, 22 to easily be attached and detached from the front portions 2, 3. A patient and/or caregiver may adjust the length of the shoulder straps 21, 22 using adjustment clips 27. A compression band 24 is located around a circumference of the bra 1 along the lower edge 34 of the bra 1 to provide compression and flexibility to the bra 1. The compression band 24 comprises an upper edge and lower edge and is preferably constructed out of an elastomeric material. Said compression band preferably comprises a plurality of sections 28 separated by stitching to make the compression band 24 wide enough to provide adequate surface area so as not to cut into the patient's skin. At least one attachment strap 4 and strap clip 9 are preferably located on the compression band 24.

Figure 4:
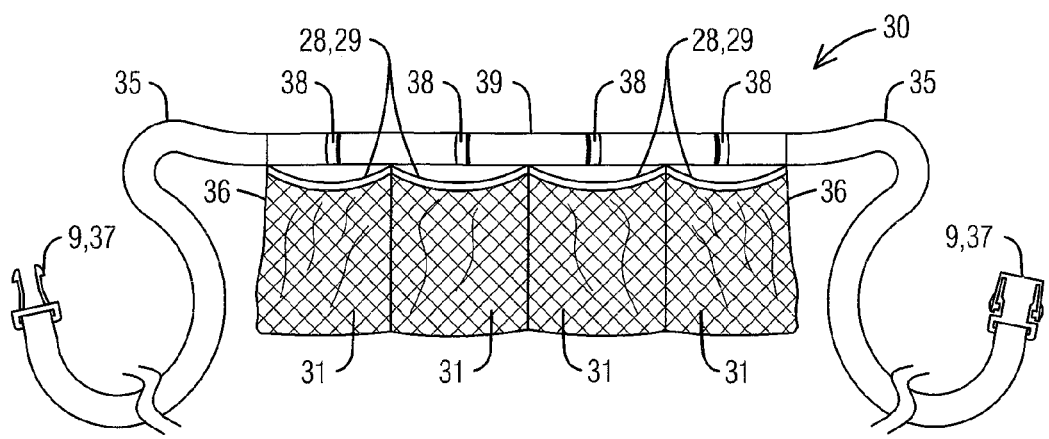
FIG. 4 is a front view of a drain apron of the present invention.
Figure 5:
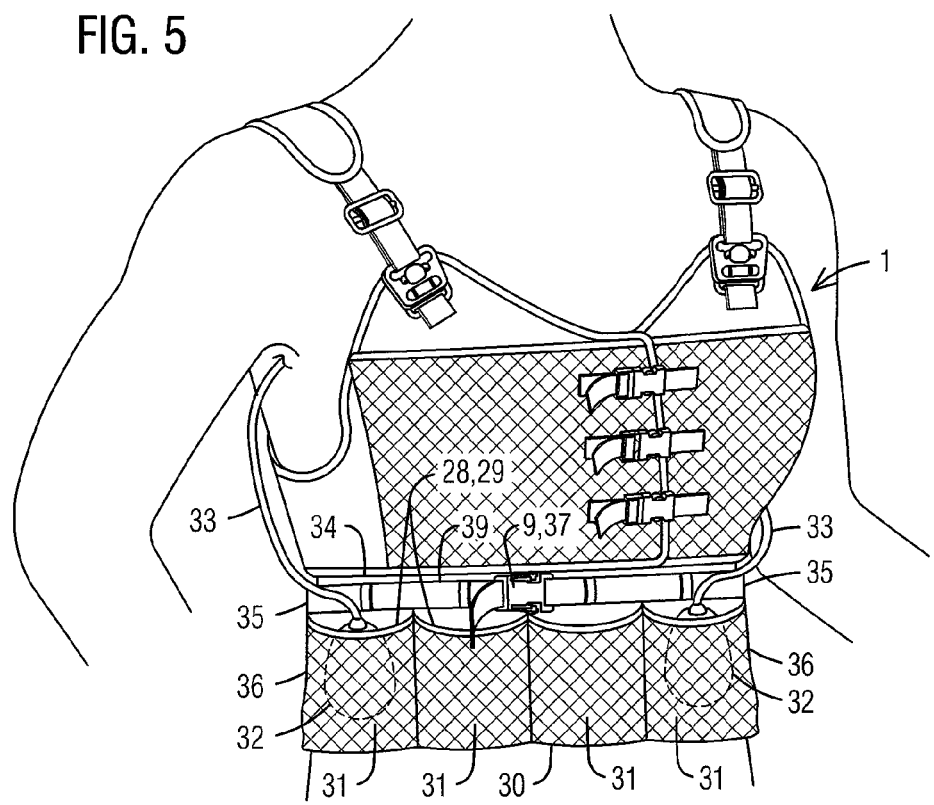
FIG. 5 is a front perspective view of a thoracic compression bra and drain apron of the present invention being worn by a patient.
Figure 6:
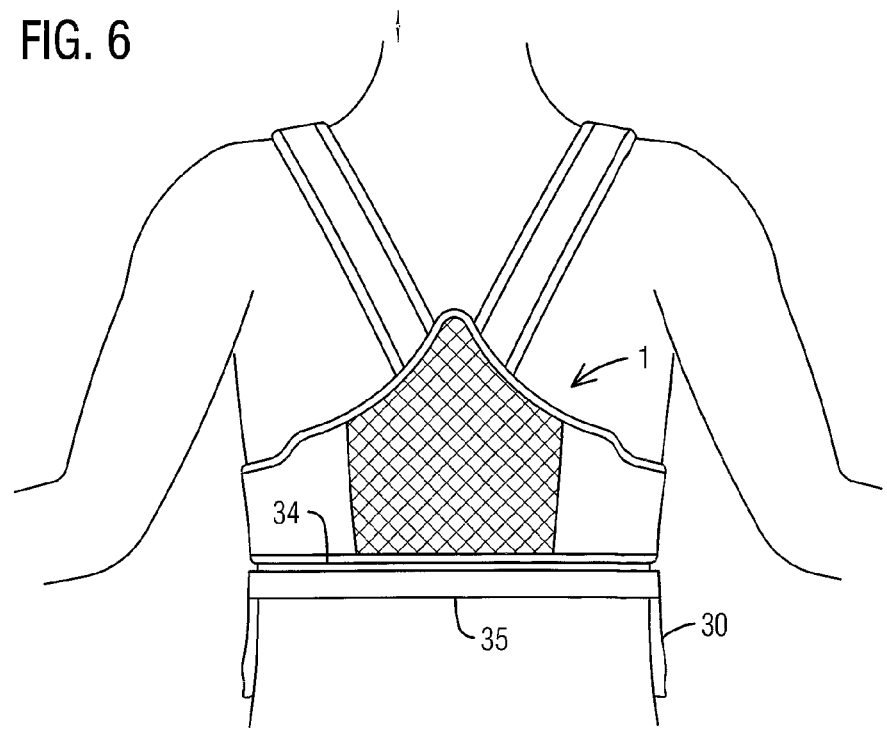
FIG. 6 is a rear view of a thoracic compression bra and drain apron of the present invention being worn by a patient.

With reference to FIGS. 4-6, a front view of a drain apron 30 of the present invention, a front perspective view of a thoracic compression bra 1 and drain apron 30 of the present invention being worn by a patient and a rear view of a thoracic compression bra 1 and drain apron 30 of the present invention being worn by a patient, respectively, are illustrated. The drain apron 30 comprises a plurality of pockets 31 located on a main panel 40 for providing storage for drain bulbs 32. Drain bulbs 32 are reservoirs connected to a flexible drainage tube 33 sutured into place. Drain bulbs 32 remove fluid from the surgical wound through mild suction. The drain apron 30 is worn around a patient's midsection, inferior to and/or extending downward from a lower edge 34 of the bra 1 either separately, removably attachable or integral to the bra 1. Straps 35 extend from side edges 36 of the drain apron 30 and are wrapped around the patient's midsection and back and secured in front of the patient, so the patient does not have to lay on an attachment means 37, such as a strap clip 9, a knot, hook and loop fastener and so forth. A plurality of loops 38 are located proximate to an upper edge 39 of the drain apron 30. The straps 35 are threaded though the loops 38 to provide additional support to the drain apron 30 and to prevent the drain apron 30 from sagging under the weight of drain bulbs 32. Elastic 29 is located along an upper edge 33 of each pocket 31 to prevent the drain bulbs 32 from falling out of the drain apron 30, which would cause unwanted pulling on the sutures holding the drain tubes 33 in the surgical wound. The pockets 31 are preferably constructed from mesh to view the contents of the pockets 31.

It is to be understood that while a preferred embodiment of the invention is illustrated, it is not to be limited to the specific form or arrangement of parts herein described and shown. It will be apparent to those skilled in the art that various changes may be made without departing from the

Having thus described my invention, I claim:

1. A thoracic compression bra for reducing the effects of swelling and bruising commonly experienced after thoracic surgery, said thoracic compression bra comprising:
   a front right portion worn over a patient's right breast and attached to a right side portion;
   said right side portion extending around a right side of a patient's torso and being attached to a rear portion that extends across a back of the patient;
   a front left portion worn over a patient's left breast and attached to a left side portion;
   said left portion extending around a left side of a patient's torso and being attached to said rear portion;
   at least one strap clip having a male portion with at least two prongs that are inserted into a female portion of the strap clip when inserted into said female portion of said strap clip to secure said male portion to said female portion to secure the front right portion to the front left portion, thereby securing the bra on the patient;
   at least one attachment strap adjustably attached to the thoracic compression bra and to the at least one strap clip so that when a distal end of the at least one attachment strap is pulled, a circumference of said thoracic compression bra is reduced, thereby compressing the front right portion and the left front portion against the right breast and left breast, respectively, of the patient.

2. The thoracic compression bra of claim 1 further comprising:
   a right shoulder strap extending from an upper edge of the rear portion to the front right portion; and
   a left shoulder strap extending from the upper edge of the rear portion to the front left portion.

3. The thoracic compression bra of claim 2 wherein:
   said right shoulder strap is attachable to said front right portion via at least one strap clip having a male portion and a female portion; and
   said left shoulder strap is attachable to said front left portion via at least one strap clip having a male portion and a female portion.

4. A thoracic compression bra for reducing the effects of swelling and bruising commonly experienced after thoracic surgery, said thoracic compression bra comprising:
   a front right portion worn over a patient's right breast and attached to a right side portion;
   said right side portion extending around a right side of a patient's torso and being attached to a rear portion that extends across a back of the patient;
   a front left portion worn over a patient's left breast and attached to a left side portion;
   said left side portion extending around a left side of a patient's torso and being attached to said rear portion;
   at least one strap clip having a male portion with at least two prongs that are inserted into a female portion of the strap clip when inserted into said female portion of said strap clip to secure said male portion to said female portion to secure the front right portion to the front left portion, thereby securing the bra on the patient;
   at least one attachment strap adjustably attached to the thoracic compression bra and to the at least one strap clip so that when a distal end of the at least one attachment strap is pulled, a circumference of said thoracic compression bra is reduced, thereby compressing the front right portion and the left front portion against the right breast and left breast, respectively, of the patient;
   a right shoulder strap extending from an upper edge of the rear portion to the front right portion; and
   a left shoulder strap extending from the upper edge of the rear portion to the front left portion.

5. The thoracic compression bra of claim 4 wherein:
   said right shoulder strap is attachable to said front right portion via at least one strap clip having a male portion and a female portion; and
   said left shoulder strap is attachable to said front left portion via at least one strap clip having a male portion and a female portion.

6. A thoracic compression bra for reducing the effects of swelling and bruising commonly experienced after thoracic surgery, said thoracic compression bra comprising:
   a front right portion worn over a patient's right breast and attached to a right side portion;
   said right side portion extending around a right side of a patient's torso and being attached to a rear portion that extends across a back of the patient;
   a front left portion worn over a patient's left breast and attached to a left side portion;
   said left side portion extending around a left side of a patient's torso and being attached to said rear portion;
   at least one strap clip having a male portion with at least two prongs that are inserted into a female portion of the strap clip when inserted into said female portion of said strap clip to secure said male portion to said female portion to secure the front right portion to the front left portion, thereby securing the bra on the patient;
   at least one attachment strap adjustably attached to the thoracic compression bra and to the at least one strap clip so that when a distal end of the at least one attachment strap is pulled, a circumference of said thoracic compression bra is reduced, thereby compressing the front right portion and the left front portion against the right breast and left breast, respectively, of the patient;
   a right shoulder strap extending from an upper edge of the rear portion to the front right portion;
   a left shoulder strap extending from the upper edge of the rear portion to the front left portion;
   said right shoulder strap is attachable to said front right portion via at least one strap clip having a male portion and a female portion; and
   said left shoulder strap is attachable to said front left portion via at least one strap clip having a male portion and a female portion.

* * * * *